US010222607B2

(12) United States Patent
Wang (10) Patent No.: US 10,222,607 B2
(45) Date of Patent: Mar. 5, 2019

(54) THREE-DIMENSIONAL ENDOSCOPE (71) Applicant: Canon USA Inc., Melville, NY (US)

(72) Inventor: Zhuo Wang, Middleton, MA (US)

(73) Assignee: Canon U.S.A., Inc., Melville, NY (US)

(*) Notice: Subject to any disclaimer, the term of this patent is extended or adjusted under 35 U.S.C. 154(b) by 128 days.

(21) Appl. No.: 15/379,109

(22) Filed: Dec. 14, 2016

(65) Prior Publication Data

US 2018/0164574 A1 Jun. 14, 2018

(51) Int. Cl.
G02B 23/24 (2006.01)
H04N 5/225 (2006.01)
(Continued)

(52) U.S. Cl.
CPC ........... *G02B 23/2415* (2013.01); *G02B 5/18* (2013.01); *G02B 23/2423* (2013.01);
(Continued)

(58) Field of Classification Search
CPC ............ H04N 13/0253; G02B 23/2415; G02B 23/2423; G02B 23/2469
See application file for complete search history.

(56) References Cited

U.S. PATENT DOCUMENTS 6,564,087 B1 5/2003 Pitris et al.
6,831,781 B2 12/2004 Tearney et al.
(Continued)

FOREIGN PATENT DOCUMENTS

EP 908849 A1 4/1999
WO 2002/38040 A2 5/2002
WO 2015/116939 A1 8/2015

OTHER PUBLICATIONS

Park, H., et al., "Forward imaging OCT endoscopic catheter based on MEMS lens scanning", Optics Letters, Jul. 1, 2012, vol. 37, No. 13.

(Continued)

*Primary Examiner* — Tsion B Owens
(74) *Attorney, Agent, or Firm* — Canon USA Inc., IP Division (57) ABSTRACT A three-dimensional (3D) endoscope is provided. The 3D endoscope comprises a probe; a positioning device to locate a tip of the probe at a first position O and a second position O'; a light guide extending through the probe and configured to guide a light propagating through the probe configured to project on a surface a first light beam from the tip at the first position and a second light beam from the tip at the second position; a detector configured to detect the first light beam reflected from the surface and the second light beam reflected from the surface; and an image processor configured to determine a first distance R between the first position and the surface based on a position difference between the first and second positions, a first deflection angle θ of the first light beam deflected from the probe at the first position and a second deflection angle θ' of the second light beam deflected from the probe; obtain image data carried by the first and second light beams detected by the detector; and obtain a 3D image based, the first distance R, the first deflection angle θ, and the first rotation angle φ associated with each pixel on the image.

20 Claims, 9 Drawing Sheets (51) Int. Cl.
*G02B 5/18* (2006.01)
*H04N 13/254* (2018.01)

(52) U.S. Cl.
CPC ..... *G02B 23/2469* (2013.01); *G02B 23/2484* (2013.01); *H04N 5/2256* (2013.01); *H04N 13/254* (2018.05); *H04N 2005/2255* (2013.01)

(56) References Cited

U.S. PATENT DOCUMENTS

| | | | |
|---|---|---|---|
| 7,304,724 | B2 | 12/2007 | Durkin et al. |
| 7,625,335 | B2 | 12/2009 | Deichmann et al. |
| 8,928,889 | B2 | 1/2015 | Tearney et al. |
| 9,254,089 | B2 | 2/2016 | Tearney et al. |
| 9,846,940 | B1* | 12/2017 | Wang ............... G06T 7/0018 |
| 2004/0222987 | A1 | 11/2004 | Chang et al. |
| 2006/0017720 | A1 | 1/2006 | Li |
| 2008/0230705 | A1* | 9/2008 | Rousso ............... A61B 5/415 250/363.04 |
| 2010/0210937 | A1 | 8/2010 | Tearney et al. |
| 2011/0275899 | A1 | 11/2011 | Tearney et al. |
| 2012/0101374 | A1 | 4/2012 | Tearney et al. |
| 2012/0190928 | A1 | 7/2012 | Boudoux |
| 2013/0093867 | A1 | 4/2013 | Schick |
| 2014/0276108 | A1 | 9/2014 | Vertikov |
| 2016/0005185 | A1* | 1/2016 | Geissler ............... G01S 5/163 348/47 |
| 2016/0316999 | A1* | 11/2016 | Lamarque .......... A61B 1/00165 |
| 2017/0020627 | A1* | 1/2017 | Tesar ................. A61B 90/20 |
| 2017/0143442 | A1* | 5/2017 | Tesar ................. A61B 90/37 |
| 2017/0180704 | A1* | 6/2017 | Panescu ............. A61B 90/37 |
| 2017/0181798 | A1* | 6/2017 | Panescu ............. A61B 34/32 |
| 2017/0280970 | A1* | 10/2017 | Sartor ............... A61B 1/0676 |
| 2018/0103246 | A1* | 4/2018 | Yamamoto ........... A61B 1/00 |
| 2018/0164574 | A1* | 6/2018 | Wang ............... G02B 23/2415 |

OTHER PUBLICATIONS

Kang, D., et al., "Spectrally-encoded color imaging", Optics Express, Aug. 17, 2009, pp. 15239-15247, vol. 17, No. 17.
Penne, J. et al., "Time-of-Flight 3-D Endoscopy", 12th International Conference, London, UK, Sep. 20-24, 2009, pp. 467-474, vol. 5761.
Thormahlen, T. et al., "Three-Dimensional Endoscopy"; Information Technology Laboratory, University of Hannover, Germany.
McLaughlin, R.A., et al., "Static and dynamic imaging of alveoli using optical coherence tomography needle probes", Journal of Applied Physiology, Sep. 15, 2012, vol. 113, No. 6.
Zeidan, A., et al, "Spectral imaging using forward-viewing spectrally encoded endoscopy", Biomedical Optics Express, Feb. 1, 2016, pp. 392-398, vol. 7, No. 2.
Zeidan, A., et al, "Miniature forward-viewing spectrally encoded endoscopic probe", Optics Letters, Aug. 15, 2014, pp. 4871-4874, vol. 39, No. 16.

* cited by examiner

Fig. 11

THREE-DIMENSIONAL ENDOSCOPE

BACKGROUND

Field of the Disclosure

The present disclosure relates in general to a spectrally encoded endoscope (SEE), and more particularly, to three-dimensional endoscope design and image reconstruction process for a spectrally encoded endoscope.

Description of the Related Art

The first endoscope was invented more than 50 years ago and consisted of a bundle of optical fibers. Since then, significant progress in minimally invasive surgeries and thereby reducing the risk of complications, costs, and recovery times has been made.

With the advent of inexpensive and miniature CMOS sensors which are mainly used in smart phones, endoscopes are shifting from fiber bundles into designs with imaging sensors at the distal tip of a probe. One significant drawback on these CMOS sensor based endoscopes is the tradeoff between the scope diameter and the resolution. The spectrally encoded endoscope (SEE) is one of the smallest endoscope that has shown a great potential for the use in minimally invasive surgeries. The original SEE system is designed for side view applications. Due to its smaller diameter of only several hundred microns, the probe itself is much more flexible compared to other scopes available on the market. However, currently, the SEE probes provide distorted two-dimensional view of a target to be imaged. It is desirable to provide a stereovision or even three-dimensional (3D) vision of the target using SEE technology without increasing the diameter of the probe.

SUMMARY

A three-dimensional (3D) endoscope is provided. The 3D endoscope comprises a probe; a positioning device to locate a tip of the probe at a first position O and a second position O'; a light guide extending through the probe and configured to guide a light propagating through the probe configured to project on a surface a first light beam from the tip at the first position and a second light beam from the tip at the second position; a detector configured to detect the first light beam reflected from the surface and the second light beam reflected from the surface; and an image processor configured to determine a first distance R between the first position and the surface and a second distance R' between the second position and the surface based on a position difference between the first and second positions, a first deflection angle $\theta$ of the first light beam deflected from the probe at the first position and a second deflection angle $\theta'$ of the second light beam deflected from the probe; determining a first and a second rotation angles $\varphi$ and $\varphi'$; obtain image data carried by the first and second light beams detected by the detector; and obtain a 3D image based on the first distance R, the first deflection angle $\theta$, the first rotation angle $\varphi$, the second distance R, the second deflection angle $\theta'$, and the second rotation angle $\varphi'$.

In one embodiment, the three-dimensional endoscope further comprises a first optical fiber extending through the probe and configured to guide the light beam propagating through the probe to project the first and second light beams. The three-dimensional endoscope also comprises a second optical fiber adjacent to the first optical fiber and configured to guide the first and second light beams detected by the detector to the image processor. The position difference of the first and second positions may include a translation $z_0$ along an z-axis along which the probe extending, and first distance R and the second distance R' may be determined based on the relationship of:

$$\frac{-z_0}{\sin(\theta - \theta')} = \frac{R}{\sin\theta'} = \frac{R'}{\sin(\pi - \theta)}$$

wherein $\theta$ is an angle of the first light beam deflected from the z-axis, and $\theta'$ is an angle of the second light beam deflected from the z-axis.

In another embodiment, the position difference may include a distance I between the first position O and the second position O' and an angle difference of the probe with the tip located at the first position and the second position. In this embodiment, the first distance R and the second distance R' may be determined based on the relationship of:

$$\frac{l}{\sin(\delta_2 - \delta_1)} = \frac{R}{\sin\delta_1} = \frac{R'}{\sin(\pi - \delta_2)}$$

wherein the l is a distance between the tip located at the first position O and the tip located at the second position O';
$\delta_2$ is an angle difference between the first light beam deflected from the probe at the first position and a vector extending through the first and second positions $\overrightarrow{OO'}$;
$\delta_1$ is an angle difference between the second light beam deflected from the tip located at the second position and $\overrightarrow{OO'}$;

The positioning device may be further configured to locate the tip of the probe at a third position. The light source is further configured to generate light propagating through the probe via a light guide to project on the surface a third light beam from the tip at the third position, such that the detector is further configured to detect the third light beam reflected from the surface at the third position. Accordingly, the image processor may determine a third distance R" between the first position and the surface based on a position difference between the first and third positions and a third deflection angle $\theta"$ of the third light beam deflected from the probe at the third position; determining a third rotation angle $\varphi"$ at the third position; obtain image data carried by the third light beam detected by the detector; and obtain the 3D image based on the first distance R, the first deflection angle $\theta$, the first rotation angle $\varphi$, the second distance R', the second deflection angle $\theta'$, the second rotation angle $\varphi'$, the third distance R", the third deflection angle $\theta"$, and the third rotation angle $\varphi"$. The system now becomes overdetermined and it is possible to solve R optimally with the consideration of measurement errors and noises.

In another embodiment, the probe comprises at least a first light guide and a second light guide, and the light source configured to generate light guided by the first light guide to project a first light beam from a tip of the first light guide onto a surface and guided by the second light guide to project a second light beam from a tip of the second light guide onto the surface. The detector is configured to detect the first and second light beams reflected from the surface. The image processor is configured to determine a first distance R between the tip of the first light guide and the surface and a second distance R' between the second light guide and the surface based on a position difference between the tips of first and second light guides, a first deflection angle $\theta$ of the first light beam projected from the tip of the first light guide, and a second deflection angle θ' of the second light beam projection from the tip at the second light guide; determine a first rotation angle φ of the first light guide and a second rotation angle φ' of the second light guide; obtain image data carried by the first and second detected light beams; and obtain a 3D image based on the first distance R, the first deflection angle θ, and the first rotation angle φ, or the second distance R', the second deflection angle θ, and the second rotation angle φ'.

A three-dimensional endoscopic image reconstruction method is provided in another embodiment. The method comprising the following steps. A first light beam is projected from a first position onto a surface, and a second light beam is projected from a second position onto the surface. The first light beam and the second light beam are reflected from the surface. A first distance R between the first position and the surface are determined based on a position difference between the first and second positions and a first deflection angle θ of the first light beam projected from the first position. A second distance R' between the second position and the surface is determined based on the position difference and a second deflection angle θ'. Image data carried by the detected first and second light beams detected by the detector are obtained; and a 3D image based on the first distance R, the first deflection angle θ, and the first rotation angle φ at the first position, or the second distance R', the second deflection angle θ', and the second rotation angle φ of the probe at the second position can be obtained.

To implement the three-dimensional endoscopic image reconstruction method, a probe is provided. A tip of the probe is located at the first position and the second position, such that the first and second light beams are projected onto the surface from the first and second positions, respectively. Alternatively, a probe including a first light guide and a second light guide is provide, and the first light beam is projected from a tip of the first light guide at the first position, while the second light beam is projected from a tip of the second light guide at the second position. The three-dimensional endoscopic image reconstruction method may also comprise projecting a third light beam from a third position onto the surface; detecting the third light beam reflected from the surface; determine a third distance R" between the third position and the surface based on a position difference between the first and third positions and a third deflection angle θ" of the third light beam projected from the third position; determining a third rotation angle φ" of the probe at the third position; obtain image data carried by the detected third light beam detected by the detector; and obtain the 3D image based on the third distance R", the third deflection angle θ" and the third rotation angle φ". The system now becomes overdetermined and it is possible to solve R optimally with the consideration of measurement errors and noises.

The three-dimensional endoscopic imaging reconstruction method according to claim 13, further comprising measuring irradiance E of the first and second light beams reflected from the surface to determine the first distance R and second distance R'.

In another embodiment, a three-dimensional endoscope is provided. The three-dimensional endoscope comprises a probe; a light guide configured to guide light. Light can propagate through the probe and a light beam is projected from a tip of the probe onto a surface; a first detector configured to detect the light beam reflected from the surface at a first position; a second detector configured to detect the light beam reflected from the surface at a second position, wherein the second position is displaced from the position with a distance $z_0$ along an axis of the probe; and an image processor configured to determine a first distance R between the first position and the surface based on a first intensity I of the light beam detected at the first position, a second intensity I' of the light beam detected at the second position, and the distance $z_0$. The first distance R is determined based on the relationship of:

$$R \approx \frac{2z_0 I \cos\theta}{I' - I}.$$

The three-dimensional imaging reconstruction discussed here may also be applied to other types of imaging reproduction scopes.

DETAILED DESCRIPTION

The following description is of certain illustrative embodiments, although other embodiments may include alternatives, equivalents, and modifications. Additionally, the illustrative embodiments may include several novel features, and a particular feature may not be essential to practice the devices, systems, and methods described herein.

Figure 1:
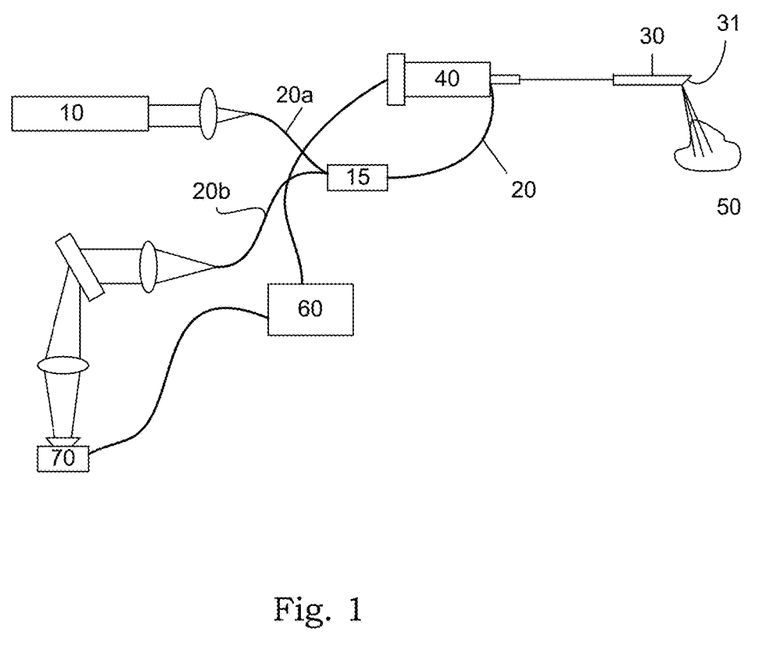
FIG. 1 is a schematic drawing of a spectrally encoded endoscopic (SEE) system and a probe according to one embodiment of this invention.

FIG. 1 shows a schematic drawing of a spectrally encoded endoscopic (SEE) apparatus. The SEE apparatus includes a light source to, preferably a broadband light source such as a supercontinuum laser coupled with a proximal end of a fiber 20a such as a single mode fiber (SMF). The distal end of the fiber 20a is attached with an SEE probe 30. The SEE probe 30 is preferably formed by attaching the fiber 20a to a focusing element to form a spot several millimeters away from a tip of the probe 30. The distal end of the SEE probe 30 includes a light dispersion element 31 to disperse the broadband light spot into a rainbow line. The light dispersion element 31 includes, for example, a grating, a prism, and other structures having the dispersion function. The sample is scanned orthogonal to the wavelength axis by rotating the SEE probe 30. As shown in FIG. 1, the rotation of the SEE probe 30 is controlled by a motor 40. The motor 40 includes, for example, a galvo motor, a step motor, a DC servo motor, etc. The diffracted light from the light dispersion element 31 is then incident on a target surface 50. The light reflected from the target surface P may be collected by another fiber 20b, for example, a multimode fiber. Three-dimensional information of image data of the target surface 50 carried by the light reflected from the target surface 50 is then analyzed by an image sensor 70. The image sensor 70, as well as the motor 40, is connected to and controlled by a computer 60. The three-dimensional information includes the three-dimensional coordinates of every point on the target surface. Based on this, it is possible to derive the location, angle, and shape of a target to be imaged. In one embodiment, the fiber 20b to collect the light reflected from the target surface 50 may be coupled with the fiber 20a for transmitting light from the light source to into the fiber bundle 20 by a coupler 15 as shown in FIG. 1. In some applications such as forward-view applications, the motor 40 may rotate continuously in one direction. A two-channel rotary junction (not shown) is needed between the motor 40 and the probe 30 if both the illumination fiber 20a and the detection fiber 20b are rotating at the same time. Alternatively, a one-channel rotary junction (not shown) between the motor 40 and the probe if only the illumination fiber 20a is rotating and the detection fiber is stationary at the tip of the probe 30.

Due to its smaller diameter of several hundred microns, the probe 30 is flexible and can be maneuvered to inspect hard-to-reach areas with a minimum bending radius of several millimeters. It is also possible to obtain color images with a modified design and the fluorescence capability. See, for example, color probes and methods as disclosed in U.S. Pat. No. 9,254,089; WO2015/116939; U.S. patent application Ser. No. 15/340,253; and U.S. Pat. App. Ser. No. 62/363,119 and fluorescence as described in U.S. Pat. No. 8,928,889 and U.S. Pat. Pub. 2012/0101374, each of which are herein incorporated by reference. The SEE apparatus as shown in FIG. 1 provides a three-dimensional vision by reconstruction of three-dimensional manifold of an image target, that is, each point in a projected two dimensional image has a three-dimensional coordinate (x, y, z). Once the information is known, it is possible to provide the stereo-vision. It also opens the avenue to perform three-dimensional feature extractions, object recognitions, and other measurements, including the measurements of volumes or surface areas, for example.

Figure 2:
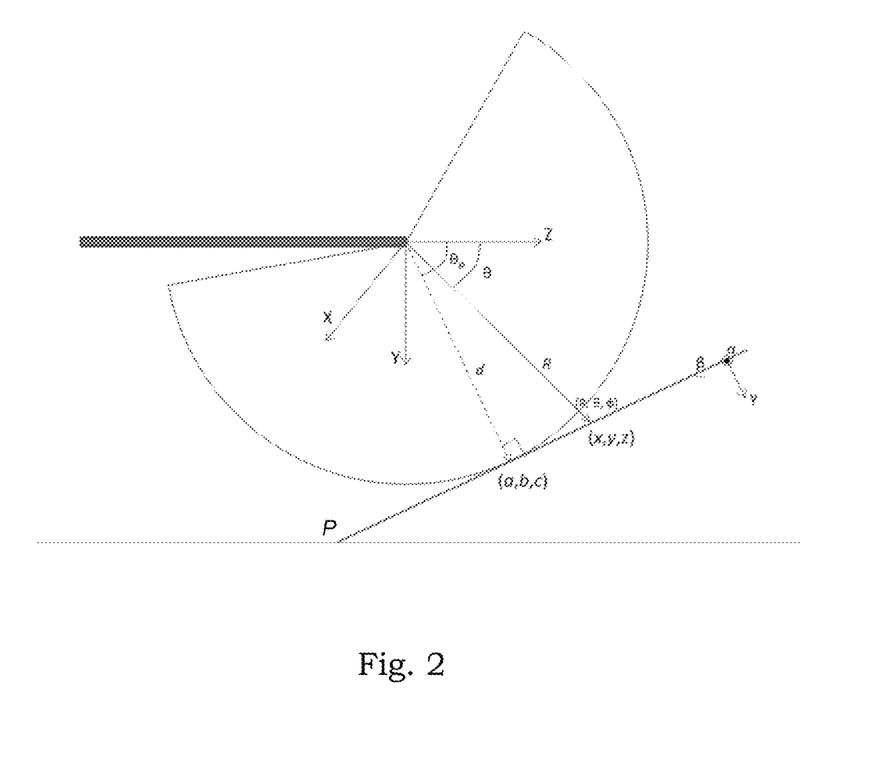
FIG. 2 shows the propagating path of the light projected from the probe of the SEE system as illustrated in FIG. 1.

FIG. 2 shows a schematic of the SEE probe to project a light beam onto a target surface and to collect the light beam reflected from the target surface. The light source to as shown in FIG. 1 generates a light traveling through the fiber 20a and the SEE probe 30. The light is then diffracted by the grating 31 and incident on a target surface, for example, the target surface P as shown in FIG. 2. The propagation path of the light may be presented by a vector in a three-dimensional affine coordinate system. Here [ ] indicates the spherical coordinate and ( ) indicates the Cartesian coordinate. The origin of the Cartesian coordinates XYZ is assumed at the tip of the SEE probe with Z-axis extending along the rotation axis of the probe. A spherical coordinate system with the same origin, that is, the tip of the probe, is also assumed with a polar angle θ measured from the fixed zenith direction Z and the azimuth angle φ of its orthogonal projection on a reference plane passing through the origin and is orthogonal to the zenith, measure from the X-axis on the plane. Any point (x, y, z) along the light ray or light beam [1, θ, φ] satisfies Equation (1):

$$\begin{cases} x = r\sin\theta\cos\phi \\ y = r\sin\theta\sin\phi \\ z = r\cos\theta \end{cases} \quad (1)$$

where r is the parameter that decides the distance of the point to the origin. The target surface P can be presented by a function of x, y, and z, that is, f (x, y, z). At the interception point of the light ray on the target surface P, $$f(x,y,z)=0 \quad (2).$$

From Equations (1) and (2), the length of the light ray, that is, the distance between the tip and the interception point of the light ray and the target surface r can be solved from Equation (2) and thus the interception point of each light ray in the three-dimension is determined. This is evident if one considers a plane in the three dimensions as:

$$(a, b, c)\begin{pmatrix} x-a \\ y-b \\ z-c \end{pmatrix} = 0 \quad (3)$$

where (a, b, c) is the surface normal to the plane as shown in FIG. 2. It is not unlikely that the light ray may intercept with a three-dimensional target surface multiple times. In such situation, the smallest positive r is preferably selected as the interception point of the light ray and the target surface P.

Figure 3:
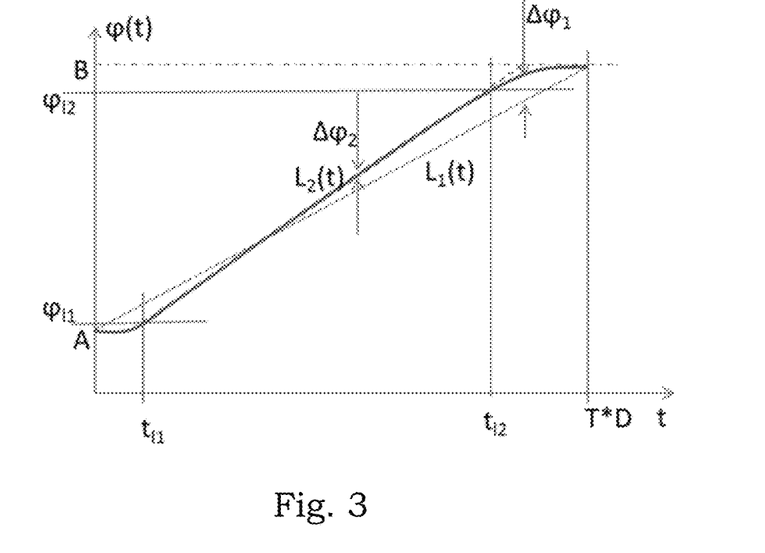
FIG. 3 is a graph showing the displacement curve of an oscillation motor driving the probe.

As discussed above, the probe 30 rotates about the z-axis. The azimuth angle φ can be determined by an encoder of the motor driving the probe, for example, the motor 40 as shown in FIG. 1. The motor may be controlled by a processor such as a computer 60 as shown in FIG. 1. FIG. 3 shows a displacement curve of a galvo motor that satisfies dφ(t)/dt≈0 at time $t_1$ (A) and time $t_2$ (B). The slope of the curve between A and B is close to a constant v. The real steps of the motor are presented by the solid line, while the ideal steps of the motor are presented by the dashed line in FIG. 3. Calibration may be needed to determine the relationship between the real scanning steps and the ideal scanning steps of the rotation of the probe. When the curve is linear, the scanning steps $\varphi_m$ satisfies:

$$\varphi_m = \frac{\Gamma}{N}\left(m - \frac{N}{2}\right) \quad (4)$$

where Γ is the total scanning angle, for example, 700 in one embodiment of the current invention, N is the number of linear portion of pixels, for example, 800, and m is the step index between 1 and N.

Figure 4:
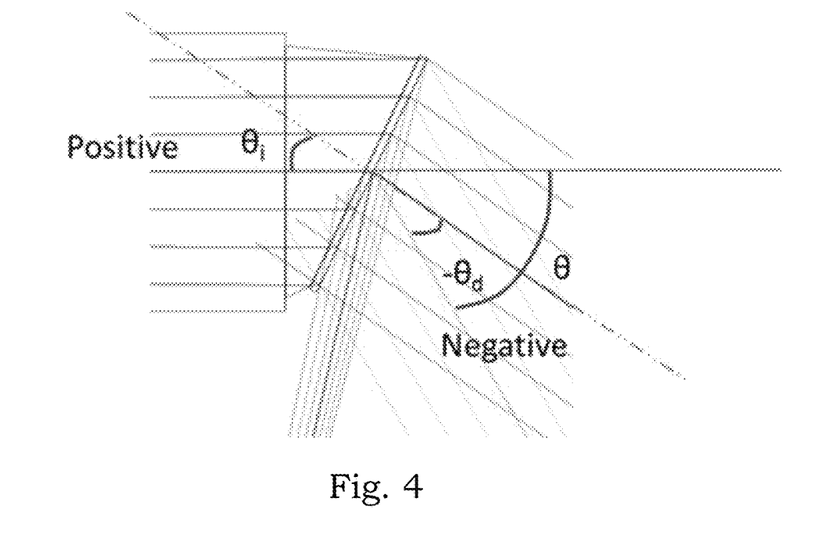
FIG. 4 shows the relationship between the incident angle and the diffractive angle of a light propagating through the grating as shown in FIG. 1.

Each wavelength of the light propagating through the grating 31 is diffracted to a distinct angle towards the target surface. Equation (5) shows the relationship between the spectral distribution of the light ray projected from the probe 30 and the incident angle and the diffractive angle of the light propagating through grating 31:

$$-n_i \sin\theta_i + n_d \sin\theta_d = mG\lambda \quad (5),$$

where $n_i$ and $n_d$ are the refractive indices of the media through which the light propagates, including the incident side and the diffractive side of the grating 31, respectively; $\theta_i$ is the incident angle of the light onto the grating 31; $\theta_d$ is the diffractive angle of the light projecting from the grating 31; m is the diffraction order, G is the grating constant of the grating 31, and λ is the wavelength of the light. The sign convention follows the definition in FIG. 4. Further, as shown in FIG. 4, the deflection angle θ as a function of the wavelength of the light satisfies the Equation (6) as:

$$\theta(\lambda) = \theta_i - \theta_d(\lambda) \tag{6}$$

Figure 5:
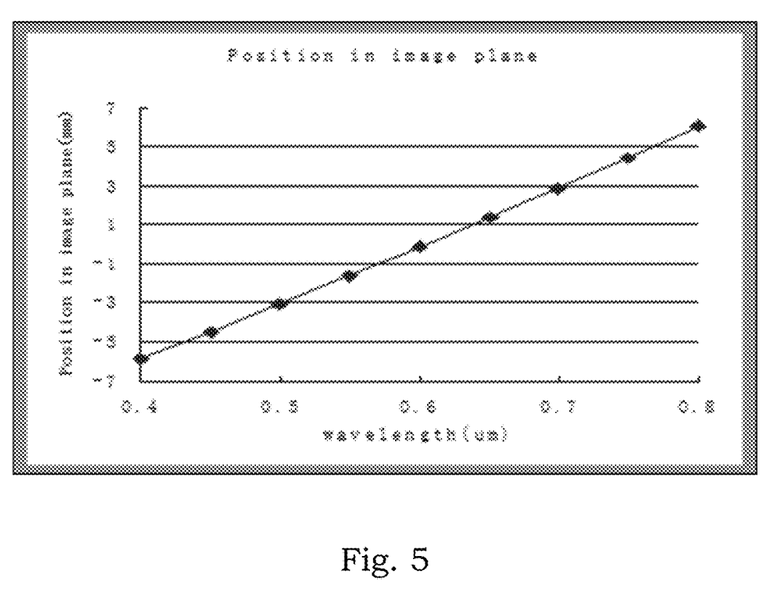
FIG. 5 shows the spectral distribution of the light at the spectrometer.

The wavelength λ of the light at the spectrometer may be calibrated based on interpolation or extrapolations from two or more wavelengths, that is, two or more color lights, and the pixel index P(λ) of each pixel by Equation (7):

$$\lambda = \frac{\lambda_2 - \lambda_1}{P(\lambda_2) - P(\lambda_1)}[P(\lambda) - P(\lambda_1)] + \lambda_1 \tag{7}$$

where $\lambda_1$ and $\lambda_2$ are the wavelengths of known spectra, for example, blue and red lasers. The linearity of the spectral distribution at the spectrometer is shown in FIG. 5. In another embodiment, three reference wavelengths, for example, blue, red, and green lasers, or even more reference wavelengths, can be applied to a polynomial for obtaining the correct relationship between the wavelengths of the collected light and the pixel indices. The mercury lamp, argon lamp or other gas lamps can be used as the reference light source as it contains abundant known spectra in the visible range and the spectral line is very fine.

Figure 6:
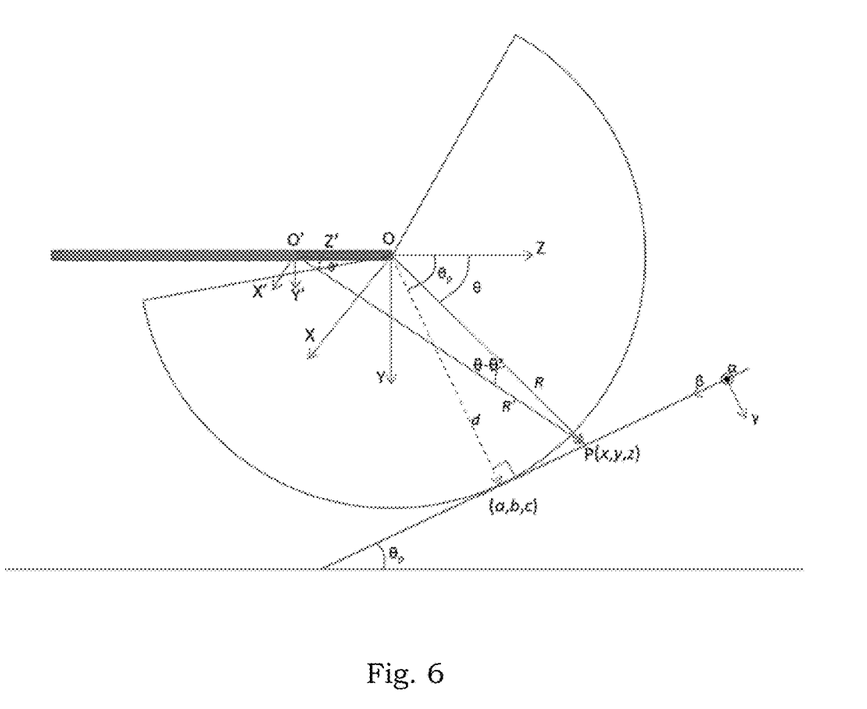
FIG. 6 shows the propagating path of the light projected from a probe for 3D image reconstruction according to one embodiment.

By applying the deflection angle θ and the azimuth angle φ obtained from Equations (4) and (6), the distance R between the tip of the probe 30 and the interception point of the light beam on the target surface P can be obtained by assuming a target surface defined by Eq. (2). If the target surface is unknown, it is also possible to reconstruct the surface mesh. Referring to FIG. 6, the tip of the probe 30 is moved from the origin O to a new position with a predetermined displacement $z_0$ along the Z-axis. A new set of coordinates X'Y'Z' with a new origin O' that overlaps with the new position of the probe tip satisfies:

$$\begin{pmatrix} x \\ y \\ z \end{pmatrix} = \begin{pmatrix} x' \\ y' \\ z' - z_0 \end{pmatrix}. \tag{8}$$

With the known variables in the triangle OO'P include θ, θ', and $z_0$, the distances R between the tip of the probe 30 at the first position and the target surface P and the distance R' between the tip of the probe 30 at the new position and the target surface P can be obtained by:

$$\frac{-z_0}{\sin(\theta - \theta')} = \frac{R}{\sin\theta'} = \frac{R'}{\sin(\pi - \theta)} \tag{9}$$

Once the distances R and R' are known, combining the known information about θ and φ, the unknown coordinates of the point of interest can be obtained as [R, θ, ρ]. 3D image construction can thus be obtained point by point from the image information carried by the light rays reflected from the interception point of the target surface, including the coordinate information discussed here.

Figure 7:
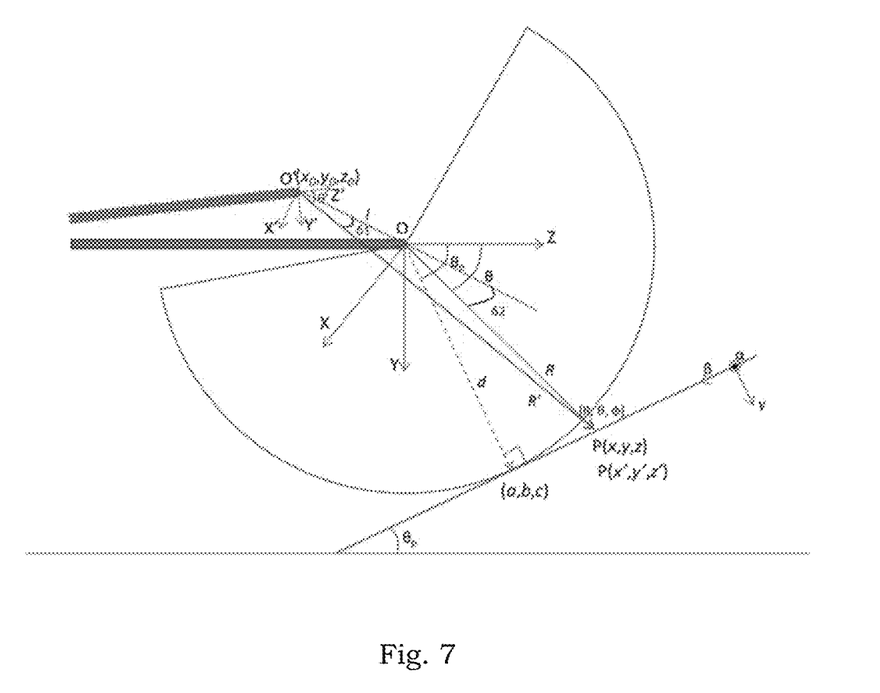
FIG. 7 shows the propagating path of light projected for a probe for 3D image reconstruction according to another embodiment.

FIG. 6 illustrates the example to obtain 3D image by projecting the light beam from two different positions along the Z-axis, that is the axis of the probe 30. In addition to the displacement along the Z-axis, the position difference may also include rotation of probe as shown in FIG. 7. The relationship between the original coordinates and the new coordinates can be presented as:

$$\begin{pmatrix} x \\ y \\ z \end{pmatrix} = C \begin{pmatrix} x' \\ y' \\ z' \end{pmatrix} + \begin{pmatrix} x_0 \\ y_0 \\ z_0 \end{pmatrix}, \tag{10}$$

where C is the transition matrix between two coordinate systems and $(x_0, y_0, z_0)$ are the coordinates of the new origin O' in XYZ coordinate system. The transition matrix C can be presented as $$\begin{bmatrix} C_{11} & C_{12} & C_{13} \\ C_{21} & C_{22} & C_{23} \\ C_{31} & C_{32} & C_{33} \end{bmatrix}$$

and calculated as:

$$(\vec{x'}, \vec{y'}, \vec{z'}) = (\vec{x}, \vec{y}, \vec{z}) \begin{bmatrix} C_{11} & C_{12} & C_{13} \\ C_{21} & C_{22} & C_{23} \\ C_{31} & C_{32} & C_{33} \end{bmatrix}. \tag{11}$$

In FIG. 7, the angles $\delta_1$, $\delta_2$, and the distance I between the origin O and O' are predetermined. The distances R and R' can be obtained by:

$$\frac{l}{\sin(\delta_2 - \delta_1)} = \frac{R}{\sin\delta_1} = \frac{R'}{\sin(\pi - \delta_2)} \tag{12}$$

With the known parameters, including $\delta_1$, $\delta_2$, R, and R', the coordinate [R, θ, φ] of the interception point of the light ray on the target surface P can be derived. 3D image construction can thus be obtained from the image information carried by the light rays reflected from the interception point of the target surface P, including the coordinate information discussed here.

Figure 8:
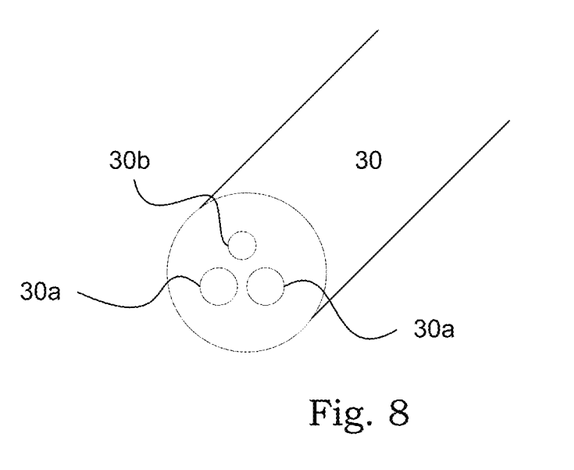
FIG. 8 shows the structure of a probe for 3D image reconstruction according to another embodiment.
Figure 8A:
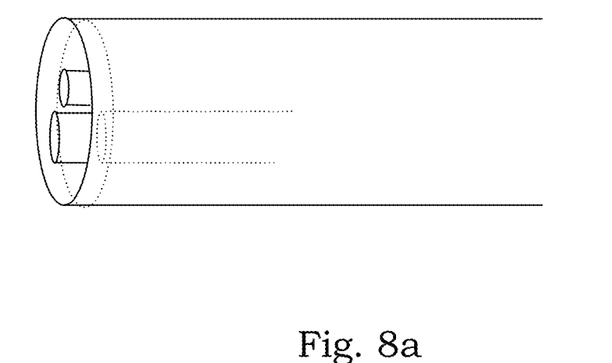
FIG. 8a is a shows a side view of FIG. 8.

Instead of moving the tip of the probe 30 at two different positions, the probe 30 may include more than one fibers extending through to project multiple light beams onto the target surface P. As shown in FIG. 8, the probe 30 may include more than one fiber 30a projecting light rays on the target surface and at least one of the fibers 30b for detecting light reflected from the target surface. As shown in FIG. 8a, the illumination fibers 30a may be offset with a known distance from each other along the axis of the probe. For this case, one can switch between these two illumination fibers 30a and overlay two images to calculate the distance and thus the 3D information. The 3D image of the target surface can be obtained in a similar manner according to Eqs. (8) and (9).

Intensity of light ray reflected from the target surface provides further information for 3D image reconstruction.

As understood, the light intensity I is a function of the distance r between the tip of the probe and the target surface as:

$$I(r') = \left[2\frac{J_1(r')}{r'}\right]^2, \quad (13)$$

where $J_1$ is the Bessel function of the first kind and the normalized radius $r'$ is given by $$r' = \frac{\pi D}{\lambda f}r = \frac{\pi r}{\lambda N},$$

Figure 9:
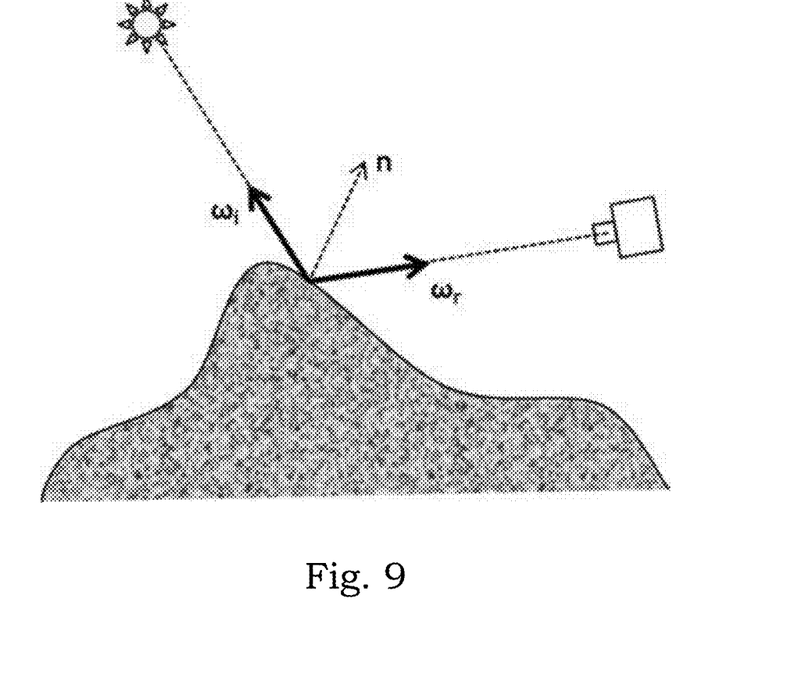
FIG. 9 is a schematic drawing showing vectors used to define bi-directional reflection distribution function (BRDF)
Figure 10:
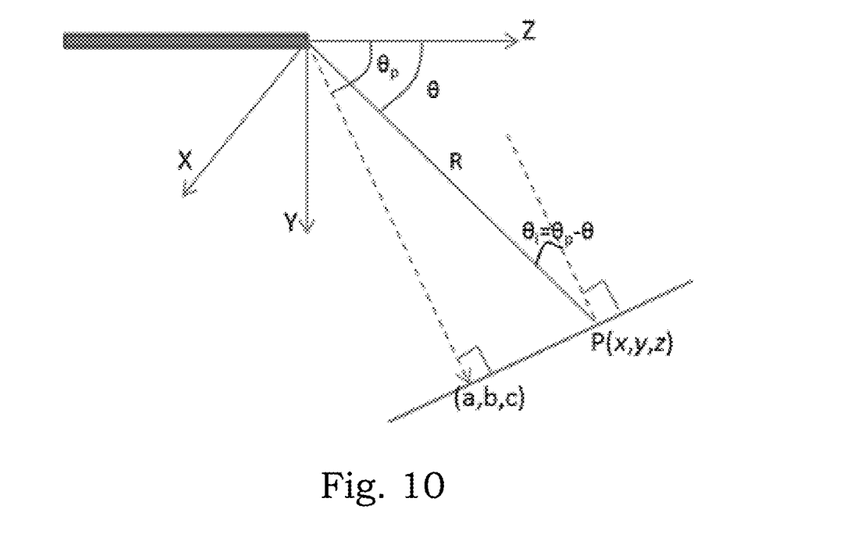
FIG. 10 shows the deviation of the power relationship for light projecting onto a target surface.

D is the aperture diameter, f is the focal length, N is f-number, and $\lambda$ is the wavelength of light. Once light intercepts with the target surface, it is reflected and collected by a detection fiber. Bi-directional reflection distribution function (BRDF) is often used for this calculation. As shown in FIG. 9, BRDF is a function of two vectors, including $\omega_i$ pointing towards the light source and $\omega_r$ pointing an image capturing device such as a camera as:

$$f_r(\omega_i, \omega_r) = \frac{dL_r(\omega_r)}{dE_i(\omega_i)} = \frac{dL_r(\omega_r)}{L_i(\omega_i)\cos\theta_i \omega_i}, \quad (14)$$

where L is radiance or power per unit solid-angle-in-the-direction-of-a-ray per unit projected-area-perpendicular-to-the ray, E is irradiance or power per unit surface area, and $\theta_i$ is the angle between $\omega_i$ and the surface normal. The index i indicates incident light, whereas the index r indicates reflected light. If the reflective surface is Lambertian, the amount of light we can collect is inverse proportional to $\cos^2\theta$.

The amount of light that can be collected is inverse square proportional to the distance between the target to the detection fiber. If we assume the image is right at the focus, the total collectable energy at the MMF (multi-mode fiber) is:

$$P \propto \frac{1}{R^4 \cos^2\theta_i}, \quad (15)$$

where R is the distance between the tip of the probe and the interception point of the light on the target surface, $\theta_i$ is the incident angle at the target surface. Equation (15) can be combined with Equation (9) to obtain more accurate solution of the distance R and R'. As the critical power P is so sensitive to the distance R, it may be sufficient to estimate the distance based on the reflective power received, assuming a fixed $\theta_i$ and proper calibrations for different tissue reflectivities (BRDFs). By varying the distance from the tip of the probe to the target by a known amount, the drop of power received provides a hint on the distance values. For example, by moving the probe away from the target to reach 1/16 of the power, the distance moved equals to R assuming the incident angle $\theta_i$ at the target surface is unchanged.

Figure 11:
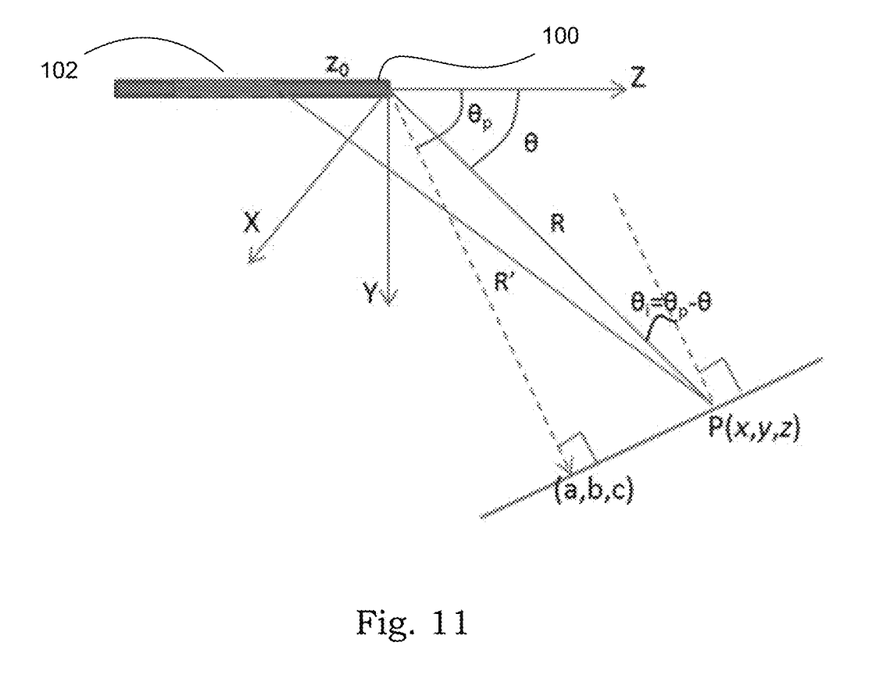
FIG. 11 shows a probe with one illumination fiber and two detection fibers for 3D image reconstruction.

FIG. 11 shows another embodiment for 3D image reconstruction. As shown, the probe includes two detection waveguides such as multimode fibers to detect light reflected from the target surface distant from each other with a displacement $z_0$ along the z-axis. The intensity I of light reached the first detector too and the intensity I' reached the second fiber 102 will be proportional to $(R'/R)^2$. Since $R' \approx R + z_0 \cos\theta$, the relationship between the intensities I and I' further satisfies:

$$\frac{I'}{I} \approx 1 + 2\frac{z_0}{R}\cos\theta \quad (16)$$

Thereby, the distance R can be derived from:

$$R \approx \frac{2z_0 I \cos\theta}{I' - I} \quad (17)$$

The distance R obtained from Equation (17) and the distance R' derived in the similar manner can be combined with Equations (9), (12), and (15) used for ensure the accuracy solution of the distances R and R'. For forward-view applications, fibers with larger NAs could be used to increase the light acceptance angle. For side-view applications, both fibers may be covered by gratings in order to accept light with very large incident angles. For both cases, the amount of light that can enter the waveguide will depend on the light detection angle $\theta$, which is also the angle between the reflected light and the surface normal of the detection fiber. A proper calibration is necessary to consider this loss together with other losses at the detection side in order to calculate the amount of light that reaches the waveguide surface I and I'. It is worth noting that what matters here is only the ratio between I and I', i.e. absolute calibration is not necessary here. It is also interesting to note that Equations (9), (12) and (15) do not contain the intensity, which means they are immune from this potential issue.

It will be appreciated that the 3D image reconstruction structure and method can be applied to non-planar target surfaces as well as planar target surfaces. The stereo vision can also be implemented based on the 3D information obtained, which is aimed to provide the depth perception and comfort for the users. The spectrum power compensation based on distances and angles, that is, critical relationship and the spot size deconvolution can also be implemented.

While the above disclosure describes certain illustrative embodiments, the invention is not limited to the above-described embodiments, and the following claims include various modifications and equivalent arrangements within their scope.

What is claimed is:

1. A three-dimensional endoscope, comprising:
   a probe;
   a positioning device configured to locate a tip of the probe at a first position O and a second position O';
   a light guide extending through the probe and configured to guide a light propagating through the probe configured to project on a surface a first light beam from the tip at the first position and a second light beam from the tip at the second position;
   a detector configured to detect the first light beam reflected from the surface and the second light beam reflected from the surface; and
   an image processor configured to:
   determine a first distance R between the first position and the surface or a second distance R' between the second position and the surface based on a position difference between the first and second positions, a first deflection angle $\theta$ of the first light beam deflected from the probe at the first position, and a second deflection angle θ' of the second light beam deflected from the probe;

determine a first rotation angle φ of the probe with the tip at the first position O and a second rotation angle φ' of the probe with the tip at the second position O';

obtain image data carried by the first and second light beams detected by the detector; and obtain a 3D image based on the first distance R, the first deflection angle θ, and the first rotation angle φ or based on the second distance R', the second deflection angle θ', and the second rotation angle φ'.

2. The three-dimensional endoscope according to claim 1, wherein the light guide comprises a first optical fiber extending through the probe and configured to guide the light beam propagating through the probe to project the first and second light beams.

3. The three-dimensional endoscope according to claim 2, further comprising a second optical fiber adjacent to the first optical fiber and configured to guide the first and second light beams to the detector and processed by the image processor.

4. The three-dimensional endoscope according to claim 3, wherein the position difference of the first and second positions includes a translation $z_0$ along an z-axis along which the probe extending, and first distance R and the second distance R' are determined based on the relationship of:

$$\frac{-z_0}{\sin(\theta - \theta')} = \frac{R}{\sin\theta'} = \frac{R'}{\sin(\pi - \theta)}$$

wherein θ is an angle of the first light beam deflected from the z-axis, and θ' is an angle of the second light beam deflected from the z-axis.

5. The three-dimensional endoscope according to claim 1, further comprising a light source configured to generate the light propagating through the light guide.

6. The three-dimensional endoscope according to claim 1, wherein the position difference includes a distance l between the first position O and the second position O' and an angle difference of the probe with the tip located at the first position and the second position.

7. The three-dimensional endoscope according to claim 5, wherein the first distance R and the second distance R' are determined based on the relationship of:

$$\frac{l}{\sin(\delta_2 - \delta_1)} = \frac{R}{\sin\delta_1} = \frac{R'}{\sin(\pi - \delta_2)}$$

wherein the l is a distance between the tip located at the first position O and the tip located at the second position O';

$\delta_2$ is an angle difference between the first light beam deflected from the probe at the first position and a vector extending through the first and second positions $\overrightarrow{OO'}$;

$\delta_1$ is an angle difference between the second light beam deflected from the tip located at the second position and $\overrightarrow{OO'}$.

8. The three-dimensional endoscope according to claim 1, wherein:

the positioning device is further configured to locate the tip of the probe at a third position;

the light guide is further configured to guide light propagating through the probe to project on the surface a third light beam from the tip at the third position;

the detector is further configured to detect the third light beam reflected from the surface at the third position; and the image processor configured to:

determine a third distance R" between the first position and the surface based on a position difference between the first and third positions and a third deflection angle θ" of the third light beam deflected from the probe at the third position;

determine a third rotation angle φ" of the probe with the tip at the first position O;

obtain image data carried by the third light beam detected by the detector; and obtain the 3D image based on, the first distance R, the first deflection angle θ, and the first rotation angle φ, the second distance R', the second deflection angle θ', and the second rotation angle φ', or the third distance R", the third deflection angle θ", and the third rotation angle φ" associated with each pixel on the image.

9. The three-dimensional endoscope according to claim 1, wherein the image processor further comprising determining the first distance R based on intensity I of the first light beam reflected from the target surface.

10. A three-dimensional endoscope, comprising:

a probe comprising at least a first light guide and a second light guide, wherein light guided by the first light guide is configured to project a first light beam from a tip of the first light guide onto a surface and guided by the second light guide to project a second light beam from a tip of the second light guide onto the surface;

a detector configured to detect the first and second light beams reflected from the surface; and an image processor configured to determine a first distance R between the tip of the first light guide and the surface or a second distance R' between the second position and the surface based on a position difference between the tips of first and second light guides, a first deflection angle θ of the first light beam projected from the tip of the first light guide, and a second deflection angle θ' of the second light beam projection from the tip at the second light guide;

determine a first rotation angle φ of the probe with the tip at the first light guide and a second rotation angle φ' of the second light guide;

obtain image data carried by the first and second detected light beams; and obtain a 3D image based on the first distance R, the first deflection angle θ, and the first rotation angle φ, or based on the second distance R', the second deflection angle θ', and the second rotation angle φ'.

11. The three-dimensional endoscope according to claim 10, wherein the first and second light guides include a first optical fiber and a second optical fiber extending through the probe, respectively.

12. The three-dimensional endoscope according to claim 11, wherein the two light guides are offset with each other by a distance $z_0$ along an z-axis the probe extending, and first distance R and the second distance R' are determined based on the relationship of.

$$\frac{-z_0}{\sin(\theta - \theta')} = \frac{R}{\sin\theta'} = \frac{R'}{\sin(\pi - \theta)}.$$

13. The three-dimensional endoscope according to claim 10, wherein the first distance R can the second distance R' are determined based on the relationship of:

$$\frac{l}{\sin(\delta_2 - \delta_1)} = \frac{R}{\sin\delta_1} = \frac{R'}{\sin(\pi - \delta_2)}$$

wherein the l is a distance between tips of the first light guide and the second light guide O and O';

$\delta_2$ is an angle difference between the first light beam deflected from the tip of the first light guide and a vector extending through the first and second positions $\overrightarrow{OO'}$;

$\delta_1$ is an angle difference between the second light beam deflected from the tip of the second light guide and $\overrightarrow{OO'}$.

14. The three-dimensional endoscope according to claim 10, wherein:
the probe further comprises a third light guide, wherein light guided by the third light guide to project a third light beam from a tip of the third light guide onto a surface;
the detector is further configured to detect the third light beam reflected from the surface; and
the image processor is further configured to
determine a third distance R" between the tip of the third light guide and the surface based on a position difference between the tips of the first and third light guides and a third deflection angle θ" of the third light beam projected from the tip of the third light guide;
determine a rotation angle φ" of the third waveguide;
obtain image data carried by the third detected light beams; and
obtain a 3D image based on the three-dimensional image data of the third distance R", the third deflection angle θ", and the third rotation angle φ".

15. The three-dimensional endoscope according to claim 10, wherein the image processor further comprising determining the first distance R based on intensity I of the first light beam reflected from the target surface.

16. A three-dimensional endoscopic image reconstruction method, comprising:
projecting a first light beam from a first position onto a surface;
projecting a second light beam from a second position onto a surface;
detecting the first light beam and the second light beam reflected from the surface;
determining a first distance R between the first position and the surface or a second distance R' between the second position and the surface based on a position difference between the first and second positions, a first deflection angle θ of the first light beam projected from the first position and a second deflection angle θ';
determining a first rotation angle φ of the probe at the first position and a second rotation angle φ' at the second position;
obtaining image data carried by the detected first and second light beams detected by the detector; and
obtaining a 3D image based on the first distance R, the first deflection angle θ, and the first rotation angle φ' or the second distance R', the second deflection angle θ, and the second rotation angle φ'.

17. The three-dimensional endoscopic image reconstruction method according to claim 16, further comprising:
providing a probe; and
locating a tip of the probe at the first position and the second position, such that the first and second light beams are projected onto the surface from the first and second positions, respectively.

18. The three-dimensional endoscopic image reconstruction method according to claim 16, further comprising:
providing a probe including a first light guide and a second light guide; and
locating a tip of the first light guide at the first position to project the first light beam therefrom and locating a tip of the second light guide at the second position to project the second light beam therefrom.

19. The three-dimensional endoscopic image reconstruction method according to claim 16, further comprising:
projecting a third light beam from a third position onto the surface;
detecting the third light beam reflected from the surface;
determining a third distance R" between the third position and the surface based on a position difference between the first and third positions and a third deflection angle θ" of the third light beam projected from the third position;
determining a third rotation angle φ" of the probe at the third position;
obtaining image data carried by the detected third light beam detected by the detector; and
obtaining the 3D image based on the third distance R", the third deflection angle θ", and the third rotation angle φ".

20. The three-dimensional endoscopic imaging reconstruction method according to claim 16, further comprising measuring irradiance E of the first and second light beams reflected from the surface to determine the first distance R and second distance R'.

* * * * *